United States Patent
Klein et al.

(10) Patent No.: US 8,231,894 B2
(45) Date of Patent: Jul. 31, 2012

(54) ANTIMICROBIAL AND IMMUNOSTIMULATING COMPOSITION

(75) Inventors: Barbara K. Klein, North Oaks, MN (US); Leo D. Katzner, Shakopee, MN (US)

(73) Assignee: Brennen Medical, Inc., St. Paul, MN (US)

( * ) Notice: Subject to any disclaimer, the term of this patent is extended or adjusted under 35 U.S.C. 154(b) by 0 days.

(21) Appl. No.: 13/156,566

(22) Filed: Jun. 9, 2011

(65) Prior Publication Data

US 2011/0244021 A1  Oct. 6, 2011

Related U.S. Application Data

(60) Continuation of application No. 11/428,929, filed on Jul. 6, 2006, now abandoned, which is a division of application No. 10/460,760, filed on Jun. 12, 2003, now abandoned, which is a continuation of application No. 09/538,655, filed on Mar. 30, 2000, now abandoned.

(51) Int. Cl.
*A61K 9/70* (2006.01)
*A61K 39/00* (2006.01)

(52) U.S. Cl. .................................. 424/443; 424/184.1
(58) Field of Classification Search ........................ None
See application file for complete search history.

(56) References Cited

U.S. PATENT DOCUMENTS

| | | | | |
|---|---|---|---|---|
| 4,837,024 A * | 6/1989 | Michaeli | ...................... | 424/446 |
| 5,326,567 A * | 7/1994 | Capelli | ........................... | 424/405 |
| 5,980,918 A * | 11/1999 | Klein | ........................... | 424/401 |
| 6,358,516 B1 * | 3/2002 | Harod | ........................... | 424/401 |
| 6,565,878 B2 * | 5/2003 | Schoenfeldt et al. | ......... | 424/443 |

\* cited by examiner

*Primary Examiner* — Suzanne Ziska
(74) *Attorney, Agent, or Firm* — Kagan Binder, PLLC

(57) ABSTRACT

A medical composition comprising an antimicrobially effective and immunostimulating amount of a combination of a β-glucan component and a silver-containing component is disclosed. The medical composition may be adapted for use topically or incorporated with a mesh material which may be further adapted for use as a wound dressing or as a surgical mesh. Methods for manufacturing the medical compositions described herein are also provided. The invention further provides methods for treating tissue damaged by wound or burn, and methods for treating or repairing tissue at a surgical site.

21 Claims, 1 Drawing Sheet

ANTIMICROBIAL AND IMMUNOSTIMULATING COMPOSITION

REFERENCE TO RELATED APPLICATIONS

This application is a continuation of pending U.S. patent application Ser. No. 11/428,929 filed Jun. 6, 2006, which is a division of abandoned U.S. patent application Ser. No. 10/460,760 filed Jun. 12, 2003, which is a is a continuation-in-part of abandoned U.S. patent application Ser. No. 09/538,655 filed Mar. 30, 2000. These three U.S. patent applications are hereby incorporated by reference in their entirety.

TECHNICAL FIELD

This invention relates generally to an antimicrobial and immunostimulating medical composition which may be adapted for use topically or as part of a mesh matrix which may be further adapted for use as a wound dressing or as a surgical mesh.

It is known to utilize immunostimulating agents as components of topical compositions, wound dressings, and surgical meshes. Examples of these uses are given in U.S. Pat. No. 5,980,918 to Klein, U.S. Pat. No. 5,676,967 to Williams et al., and U.S. patent application Ser. No. 09/406,551 also to Klein, respectively. U.S. Pat. Nos. 5,980,918 and 5,676,967, and U.S. patent application Ser. No. 09/406,551 are all assigned jointly with the present application and are hereby incorporated by reference.

There is a need with respect to all topical compositions, wound dressings and surgical meshes to provide an effective antimicrobial function in addition to the immunostimulating function described above.

This and other objectives and advantages of the invention will appear more fully from the following description, made in conjunction with the accompanying drawings wherein like reference characters refer to the same or similar parts throughout the several views.

SUMMARY OF THE INVENTION

The present invention provides a medical composition that has the immunostimulating properties common to the topical compositions, wound dressings, and surgical meshes described in the aforementioned patents and patent application, along with antimicrobial properties that aid in preventing or alleviating infection. Consequently, a medical composition according to the present invention comprises an antimicrobially effective and immunostimulating amount of a combination of a β-glucan component and a silver-containing component.

The β-glucan component is suitably derived from a cereal such as oats, wheat or barley, but may also be derived from yeast, bacteria, and fungus. The medical composition of the present invention may suitably include a cereal-derived β-D-glucan derived from one of wheat, oats, and barley. An especially beneficial form of β-D-glucan is characterized as (13) (1-4) β-D-glucan derived from oats, wheat, or barley.

The silver component of the medical composition is suitably chosen from a group comprising elemental silver, silver nitrate, silver bromide, silver sulfate, silver fluoride, silver iodide, silver chloride, silver oxides, silver protein, silver lactate, silver citrate, and silver sulfadiazine.

A topical composition formulated according to the principles of the present invention may take the form of an unguent, a cream, a gel, an emollient, an oil or a lotion.

The medical composition of the present invention may form a layer of a biocompatible surgical mesh or may be impregnated into a mesh matrix of such a surgical mesh.

Similarly, the medical composition may also form a layer of a wound dressing or may be impregnated into a mesh material of a wound dressing. A wound dressing comprising the medical composition of the present invention may include a mesh material that has a coating that includes a β-glucan compound and elemental silver or a silver compound. The wound dressing may include a polymeric film of vapor-permeable material bonded to one side of the coated mesh material, as an exterior surface of the wound dressing.

Methods for manufacturing the medical compositions described herein are also provided. The invention further provides methods for treating tissue damaged by wound or burn, and methods for treating or repairing tissue at a surgical site.

DETAILED DESCRIPTION OF THE INVENTION

Medical Composition

Figure 1:
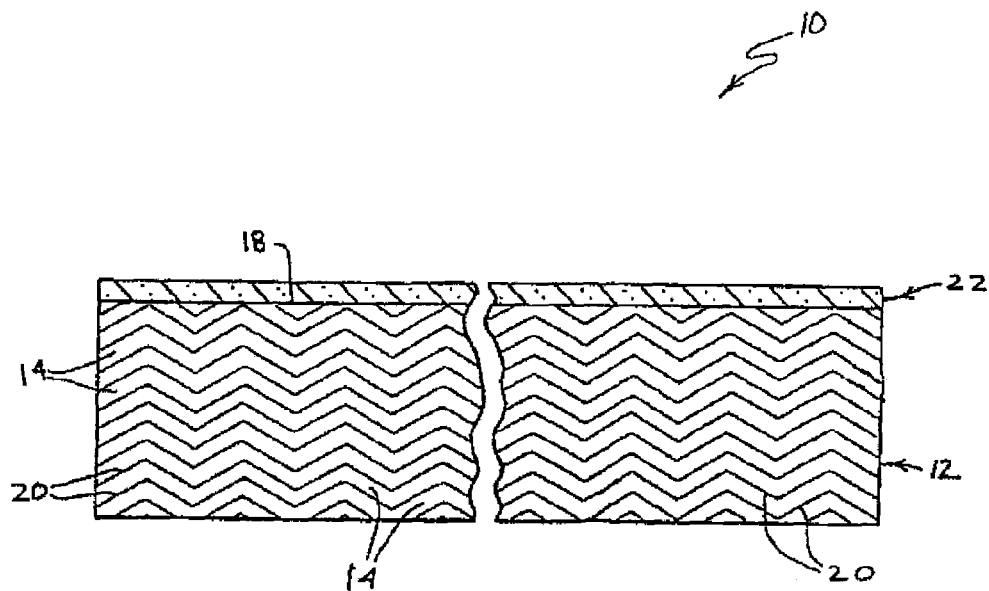
FIG. 1 is a side view of a wound dressing incorporating the medical composition of the present invention.

Each of the components of the medical composition described herein serves a particular function or functions, and is available in purities conducive for use in the particular applications. Thus, a component may comprise United States Pharmacia (USP), National Formulary (NF), or other purified grade appropriate for topical use on burns and wounds on the skin, or for internal use when required.

The medical compositions of the invention may be prepared from the stated components, and any other additives, using conventional methods.

The preferred active ingredients of the medical composition of the present invention are a β-glucan compound and a silver compound.

β-Glucan Component

Compounds classified as β-glucans comprise a large group of higher molecular weight polymers containing glucopyranosyl units in n-linked chains. β-glucans are found in essentially all living cells that are enclosed by cell walls and have considerable structural variation depending on the source. β-glucans are highly unbranched homopolysaccharides and are isomerically disposed to α-D-glucan (e.g., starch), which is typically non-functional as a structural support component of the cell. β-glucans generally comprise a large number of glucopyranosyl units linked primarily by (1-3) and (1-4) linkages. Various types of β-glucans are described in U.S. Pat. No. 5,980,918 to Klein, which was incorporated by reference above.

As described in U.S. Pat. No. 5,980,918, β-glucans have a strong immunostimulating property, which makes them ideal for use in medical compositions applied to wounds and surgical sites. The β-glucans actually stimulate the immune response of the tissues at the wound or surgical site, which has the effect of improving tissue regeneration and speeding recovery.

The primary source of β-glucan compounds has historically been yeast and bacterial cells. The most readily available types of β-glucans presently are those derived from yeast, bacteria, and fungi and from cereal grains such as wheat, barley, and oats. All of these β-glucans may be used to formulate the medical composition of the present invention.

Cereal-derived β-D-glucan is significantly different from β-glucans obtained from other sources, including β-D-glucans derived from yeast such as *Saccharomyces cerevisiae* and bacteria such as *Cellulomonas flavigena*. The cereal-derived (1-3)(1-4) β-D-glucan is distinctive from microbial-derived glucans, which have all (1-3) linkages or primarily (1-3) linkages with a few (1-6) linkages.

The molecular weight of the mixed-linkage cereal-derived β-glucan suitable for use in this invention is generally much greater than that of microbial-derived glucans. Suitable cereal-derived β-glucan compounds may span a fairly broad range of molecular weights, i.e., from about 1 kDa to about 1,500 kDa, and preferably from 200 kDa to 700 kDa.

As further described in U.S. Pat. No. 5,980,918, cereal derived β-glucans have been shown to be the most efficacious in stimulating the immune response of the tissues at a wound or surgical site. Therefore, it is preferred to utilize cereal-derived β-glucans such as those derived from wheat, barley and oats as the β-glucan component of the medical composition of the present invention. Cereal-derived glucan (CDG) may be characterized as follows:

a. CDG is a long chain, unbranched polysaccharide that typically makes up about 3-4% of oat and barley grains. The CDG concentration is greater, e.g. 7-10%, in the milled bran fraction of oats.

b. CDG is found in the endosperm and aleurone cell walls of most cereal grains. The microbe-derived glucans occur in the cell wall of the yeast or bacteria.

c. CDG is a mixed-linkage molecule containing about 70 percent (1-4)-linkages and about 30 percent (1-3)-linkages. The (1-3)-linked units mostly occur singly whereas the (1-4)-linked units typically occur in groups of three or four glucopyranosyl units. Thus, the resultant structure is a series of short runs of 3 or 4 (1-4)-linked glucopyranosyl units, adjacent runs connected by (1-3) linkages. The frequencies of the groups of three (cellotriosyl) and four (cellotetraosyl) glucopyranosyl units also tend to be characteristic of the source, being affected by cereal variety, tissue age, and stage of maturity. Oat-derived CDG typically has more of the groups of three consecutive (1-4)-linked glucopyranosyl units than does barley-derived CDG. The ratio of trisaccharide to tetrasaccharide groups is about 2:1 for oats and closer to 3:1 for barley. CDG differs from microbe-derived glucans, which have all (1-3)-linkages or mostly (1-3)-linkages with some (1-6)-linkages.

d. CDG is a linear molecule, while yeast-derived glucan forms a helical shape.

e. The degree of polymerization of CDG is in the range of about 1200-1800. On the other hand, yeast-derived β-D-glucan has a much lower degree of polymerization, i.e. about 60-80. Cellulose, the primary constituent of plant cell walls, has all β(1-4) linkages and a degree of polymerization of about 10,000 to 15,000.

f. CDG forms viscous solutions in warm water. In contrast, yeast-derived glucan is insoluble in water but dispersible in aqueous systems.

g. CDG occurs within the grain with a fairly broad range of molecular weights, i.e. about 200 kDa to about 700 kDa. The molecular weight is believed to be dependent upon the grain species, grain source, glucan extraction conditions and particular laboratory. Microbe-derived glucan has a much lower molecular weight, in the range of about 10 kDa to about 14 kDa. Cellulose has a molecular weight of about 700 kDa.

h. The use of CDG as a food component has been studied extensively by various researchers; studies have included the use of CDG in regulation of glucose metabolism, hypoglycemic response, reduction in serum cholesterol, and the like.

Thus, in terms of chemical structure and molecular weight, CDC is much more like cellulose than are the microbial-derived glucans.

The preferred active agent is β-D-glucan derived from oats, although the glucans from barley, wheat and/or other cereal grains may be used for the topical composition, provided the β-D-glucan can be extracted economically.

Silver-Containing Component

The second active ingredient of the medical composition of the present invention is a silver-containing component providing antimicrobial properties. The silver-containing component may be a silver compound or other source of silver that is capable of releasing elemental silver or silver ion in situ.

Silver-containing components suitable for use with the medical composition of the present invention act to kill or inhibit the growth of bacteria or other infectious agents that may be present at a wound or surgical site. Silver-containing components suitable for use with the medical composition of the present invention comprise elemental silver, or silver compounds including inorganic silver salts such as silver nitrate, silver bromide, silver sulfate, silver fluoride, silver iodide, silver chloride and silver oxides, and organic silver salts such as silver protein (mild and strong), silver lactate, silver citrate, or silver sulfadiazine. It is to be understood that this is not an exhaustive list of the silver compounds which may be used with the medical composition of the present invention and that other silver compounds may suitably be used. Furthermore, mixtures of silver compounds, or a silver compound and elemental silver, may also be suitable. Silver metal, such as silver foil or colloidal silver, may also be suitable in some embodiments.

Topical Compositions

The medical composition of the present invention may be included as a component of a topical composition of the type described in U.S. Pat. No. 5,980,918. In use, such a topical composition is preferably applied directly to a wound or to a surgical site so that the immunostimulating and antimicrobial properties of the topical composition may work in conjunction to stimulate healing. A topical composition which comprises the medical composition of the present invention may be formulated in various ways including those topical composition variously known as unguents, creams, gels, emollients, lotions and oils, each with a generally characteristic solvent composition and having a form ranging from liquid to semi-solid. A topical composition may be applied directly by rubbing the composition onto the desired treatment area, or may be applied indirectly such as by coating the composition onto an applicator, a wound dressing, or other means of application.

A topical composition of the invention may contain, for example, about 0.05% to about 15% by weight of a β-glucan component, and about 0.05% to about 70% by weight of a silver-containing component. In some embodiments, the topical composition contains about 0.05% to about 15% by weight of a β-glucan component, and about 0.05% to about 15% by weight of a silver-containing component. A particularly suitable combination is about 0.05% to about 15% by weight of (1-3)(1-4) β-D-glucan component, and about 0.05% to about 15% by weight of silver nitrate.

In addition to the β-glucan component and silver-containing component, a topical formulation may include one or more of an ointment base, a solvent, a suspending/viscosity increasing agent, an emulsifying/solubilizing agent, a stiffening agent, an emollient, and a preservative. Other additives known in the art, such as plasticizers, humectants, etc. may also be suitable.

A suitable ointment base may include white petrolatum, cod liver oil, mineral oil, shark oil, paraffin, lanolin, cetyl alcohol, and/or cetyl ester wax, and the like.

In formulations comprising a solvent, the solvent may suitably be primarily or entirely water. Additional solvents which may be added at generally lower concentrations include natural oils such as cod liver oil, mineral oil, etc., and glycerol or propylene glycol. In some embodiments, the water content of a cream or gel formulation is at least about 50% by weight.

A suspending/viscosity increasing agent, such as carrageenan, may be suitably included in a topical composition comprising a solvent. Other possible suspending/viscosity increasing agents include polyvinyl alcohol, xanthan gum, agarose, alginate, guar gum, a carbomer such as CARBOPOL 940 (Noveon, Inc., Cleveland, Ohio), and carboxymethylcellulose, as well as mixtures thereof. A variation in the concentration of suspending agents is compensated by varying the solvent concentration.

A stiffening agent useful in forming a topical composition with the medical composition of the present invention may comprise cetyl alcohol, cetyl esters wax, or paraffin.

A suitable emulsifying/solubilizing agent may suitably include sodium lauryl sulfate or non-ionic emulsifiers such as glyceryl stearate, PEG 100 stearate and triethanolamine.

A suspending/viscosity increasing agent suitable for use with the medical composition may suitably include polyvinyl alcohol, agarose, alginate, xanthan gum, guar gum, sodium carboxymethylcelluloses, or carbomer.

A preservative such as methyl paraben, ethyl paraben, butyl paraben, propyl paraben, benzalkonium chloride, benzoic acid, benzoic alcohol, imidurea, or diazolidinyl urea may also suitably be used in a topical composition formulated according to the present invention.

An ointment according to the present invention may comprise about 50% to about 99.5% by weight of petrolatum or alternate ointment base.

A lotion or cream of the present invention may include, for example, a cereal-derived β-glucan compound, a solvent, an emulsifying/solubilizing agent, a suspending/viscosity increasing agent, and a preservative.

A specific formulation of a topical composition comprising the medical composition of the present invention and taking the form of a lotion may include 0.05-15 w/w % oat-derived β-D-glucan and 0.05-15 w/w % silver nitrate ($AgNO_3$). Additional components may include: 20-90 w/w % water, 3-60 w/w % petrolatum, 2-30 w/w % glycerol stearate, and 2-20 w/w % PEG 100 stearate.

Another formulation of a topical composition for application to the skin and mucosa for treating burns and wounds and other skin loss injuries and conditions comprises 0.05-15 w/w % β-D-glucan and a silver-containing component as active ingredients in a cream base, gel base or oil base.

Another formulation of a topical composition comprising the medical composition takes the form of a cream and includes β-glucan, a solvent including water, an ointment base, an emulsifying/solubilizing agent, a suspending/viscosity increasing agent, and a preservative. Preferably, at least 20 w/w % of the topical composition of this formulation will be solvent. The solvent may include an emollient such as glycerol or propylene glycol. The ointment base typically makes up 3-60 w/w % of the topical composition and may comprise petrolatum, cod liver oil, mineral oil, shark oil, paraffin, lanolin, cetyl alcohol, and/or cetyl ester wax.

A suitable gel formation including the medical composition of the present invention comprises a gel base generally including water, at least one suspending/viscosity increasing agent, and optionally a preservative mixed with the medical composition. The suspending/viscosity increasing agent(s) is typically chosen from a group that includes polyvinyl alcohol, sodium carboxymethylcellulose, xanthan gum, agarose, alginate, guar gum, and carbomer. The suspending/viscosity increasing agent(s) may include one or more of the aforementioned group. Such a gel preferably has a water base including at least about 50 w/w % water. More specifically, such a gel may comprise about 50-98 w/w % water and about 0.5-15 w/w % suspending/viscosity increasing agent(s).

By way of example, and without limiting the forms that a topical composition comprising the medical composition of the present invention may take, a specific formulation of a lotion comprising the medical composition of the present invention was made as follows: An aqueous solution of oat derived β-glucan was prepared by dissolving 2 grams of oat derived β-glucan in 165 grams of water at 95° C. A separate oil-phase solution was prepared by mixing 20 grams petrolatum with 10 grams of a (49% glycerol stearate/51% PEG 100 stearate) blend. This blend may be replaced by equal amounts of the respective constituents or by an equivalent compound. The oil phase solution was heated to 65° C. and added to the aqueous solution which had been cooled to, and held at, 65° C. The mixture of the oil phase and aqueous solutions was emulsified for two minutes at 27,000 RPM in a mixer. Three grams of silver nitrate were then added and emulsification continued for an additional one minute. The weight percentages (w/w %) of the components of the prepared lotion where as follows:

| | |
|---|---|
| β-D-glucan (oat-derived) | 1% |
| Silver nitrate | 1.5% |
| Water | 82.5% |
| Petrolatum | 10% |
| Glycerol Stearate | 2.5% |
| PEG 100 Stearate | 2.5% |
| Total | 100.0% |

Wound Dressing

The medical composition of the present invention may be used in fabricating wound dressings that provide both immunostimulating and antimicrobial properties. The medical composition of the present invention may, for example, be added to a mesh wound dressing of the type disclosed in U.S. Pat. No. 5,676,967 to Williams, et al. incorporated by reference above. In such a wound dressing, the medical composition containing a β-glucan component and a silver-containing component would be used to impregnate a mesh material. The wound dressing may also include a vapor-permeable layer which is occlusive to moisture and bacteria.

As used herein, the term "mesh" and phrase "mesh material" refer to a woven, nonwoven, or film material suitable as a substrate to which the medical composition of the present invention may be applied. A mesh material may be of synthetic, animal, human, plant, or mineral origin. Synthetic materials from which a suitable mesh may be fabricated include polyester, polypropylene, polytetrafluoroethylene, expanded polytetrafluoroethylene, polyurethane, polyethylene terephthalate, polyglycolic acid, polyglactin, and silicone. Other types of meshes may be used, including but not limited to gauzes and organic meshes, and polymeric films.

Suitable organic surgical meshes that may be combined with the medical composition of the present invention may be derived from human sources, animal sources, and cadaveric sources. Homologous mesh materials may be derived from the tissues of a donor, from animal tissues, or from cadaveric tissues. Autologous mesh materials are derived from a patient's own body, and may comprise dermographs, fascia tissues, and dura mater.

For the wound dressing, an optional polymeric film may be applied to the mesh material. The polymeric film is suitably a vapor-permeable material. Preferably, the film has a moisture-vapor transmission rate (MVTR) in a range suitable for medical or wound-dressing applications. By way of example, a MVTR of about 1500 g/m$^2$/24 hours or greater is desirable, although a film having a lower MVTR may also be suitable in some embodiments.

With reference to the FIG. 1, wound dressing 10 comprises an impregnated mesh material. The mesh material is preferably a multifilament woven mesh netting 12 formed of thin polyester fibers 20, though other types of meshes may be used, including but not being limited to gauzes, synthetic meshes, and organic meshes (of both autologous and homologous sources). The mesh netting material 12 has a structure with holes or openings 14 that permit a solution containing the medical composition of the present invention to impregnate the mesh netting material 12.

The wound dressing 10 may also comprise a vapor-permeable layer 22, which is occlusive to moisture and bacteria. The vapor-permeable layer 22 may be made, for example, of a film of butylene/poly(alkylene ether) phthalate plus stabilizer, and joined to surface 18 of the mesh netting material 12 by a thermal process or other means, and acts to prevent moisture and bacteria from entering the wound while allowing vapor to pass through the dressing 10 from the wound site into the air.

The β-glucan component of the medical composition is applied to the mesh material of the wound dressing to produce a concentration equal to about 0.01-50% of the dressing's dry weight, in some embodiments. The silver-containing component of the medical composition is applied to the mesh material of the wound dressing to produce a concentration equal to about 0.01-15% of the dressing's dry weight, in some embodiments.

Additional components of the wound dressing may include a coating of a collagenic protein. The optional collagenic protein component of the wound dressing may include a mixture of Type I and Type III collagens that makes up 0.1-20% of the dry weight of the dressing, for example. Collagen is commercially available in several forms. While other collagenic protein materials may be used, a readily available material comprising a mixture of Type I and Type III collagens is a lyophilized, soluble, collagen fiber-like powder extracted from bovine hides. Type II and/or Type IV collagens may also be used, but their lower solubility, higher hydrophobicity makes their controllable application as a suspension to fibers more difficult, and their subsequent transport into the wound proceeds at a lower rate.

Another embodiment of a wound dressing which incorporates the medical composition of the present invention may comprise a polyester mesh netting formed of a woven monofilament polyester having a thickness of about 0.01-0.05 inches. To this netting is applied a coating that includes a β-glucan compound and a silver compound that are mixed with a collagenic protein in a ratio of 1:100 to 100:1 on a dry weight basis.

By way of example, a wound dressing which comprises the medical composition of the present invention was made as follows: An aqueous solution of oat-derived β-glucan and silver nitrate was prepared. The solution contained 1.0 wt % β-glucan and 0.3 wt % silver nitrate. This aqueous solution was used to impregnate the mesh netting of the dressing. The aqueous solution in the mesh netting of the dressing was then dehydrated at 25° C. Following dehydration, the completed wound dressing with the impregnated mesh netting was packaged and sterilized. The weight percentages (w/w %) of the compounds of the resulting exemplary wound dressing were as follows:

| | |
|---|---|
| β-D-glucan (oat derived) | 31.3% |
| Silver nitrate | 9.8% |
| Mesh netting | 58.9% |
| Total | 100.0% |

Surgical Meshes

The medical compositions of the present invention may also be used in producing a biocompatible mesh device for treating or repairing tissue at a surgical site. Surgical meshes are porous, gauze-like sheet materials which may be woven or spun from a variety of organic and synthetic materials. Examples of biocompatible surgical meshes incorporating fl-glucan are given in U.S. patent application Ser. No. 09/406,551 to Klein, incorporated by reference above. The biocompatible mesh device of the present invention comprises the medical composition described above, and a mesh matrix.

The phrase "mesh matrix" is used herein to refer to a biocompatible woven or nonwoven mesh material. The material from which a surgical mesh is made must be biocompatible, chemically and physically inert, non-toxic and non-carcinogenic, is preferably mechanically strong, and easily fabricated and sterilized.

Most synthetic surgical meshes are woven from monofilament or multifilament fibers to form a mesh having pores of varying sizes and geometries. Other synthetic surgical meshes are formed in a node-and-fibril arrangement in which the mesh includes larger sections, or nodes, which are interconnected by fibrils of the mesh material.

Synthetic materials from which a biocompatible mesh matrix may be fabricated include polyester, polypropylene, polytetrafluoroethylene, expanded polytetrafluoroethylene, polyurethane, polyethylene terephthalate, polyglycolic acid, polyglactin, and silicone. Other types of meshes may be used, including but not limited to gauzes and organic meshes. Suitable organic surgical meshes that may be combined with the medical composition of the present invention may be derived from human sources, animal sources, and cadaveric sources. Homologous mesh materials may be derived from the tissues of a donor, from animal tissues, or from cadaveric tissues. Autologous mesh materials are derived from a patient's own body, and may comprise dermographs, fascia tissues, and dura mater.

Figure 2:
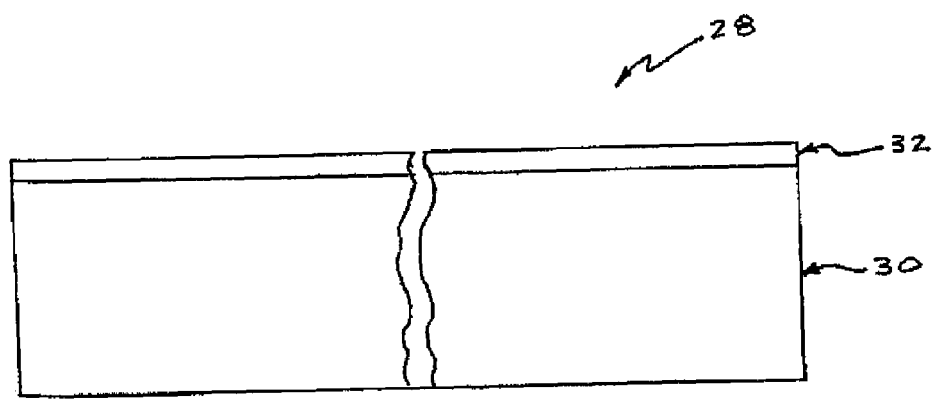
FIG. 2 is a side view of a surgical mesh incorporating the medical composition of the present invention.

With reference to FIG. 2, a surgical mesh 28 typically takes the form of porous, gauzelike sheet of material 30, which may be made from various organic materials (of both autologous and homologous sources) or synthetic materials. In general, the surgical mesh will be an implantable device, and may be suitable for providing reinforcement to a damaged tissue. The most common use of surgical meshes involves the reinforcement of herniations. Surgical meshes are also used in gynecological procedures including abdominal sacrocolopopexy and as suburethral slings. Other procedures which require surgical meshes include laparoscopic retropubic urethropexy, intraperitoneal placement for adhesion prevention, the repair of pelvic floor hernias, rectoceles, and cystoceles. It is to be understood that the aforementioned surgical procedures do not comprise a complete list of all uses of organic and synthetic surgical meshes. New and varied uses for surgical meshes are being discovered on an ongoing basis and the present invention is to be construed to be applicable to all present and future uses of surgical meshes.

In many surgical procedures, it is desirable that a surgical mesh becomes incorporated into the tissues surrounding a surgical site. One example of such a surgical procedure is the reinforcement of a herniation. In the repair of a hernia, and after the hernia has itself been closed using standard surgical techniques, a surgical mesh of appropriate size and shape is placed over the newly repaired hernia and secured in place using sutures, staples, surgical adhesives, or any other suitable connecting means. As the tissues surrounding the surgical site heal, granulation tissues growing at and around the surgical site begin to produce an extracellular matrix which, in a process called fibrosis, infiltrates and attaches to the material of the surgical mesh secured over the surgical site. Incorporation of the surgical mesh into the surgical site by the extracellular matrix strengthens the tissues at the surgical site and helps prevent re-injury.

Preferably, the medical composition of the present invention will be used to impregnate a mesh matrix in the same manner as described above for the wound dressing of the present invention. However, as illustrated in FIG. 2, it is also possible that the medical composition may be constituted as a film that is applied as a discrete layer 32 to one or both sides of the surgical mesh 28 by a thermal process or by other means.

Methods for Treating Tissue Damaged by Wound or Burn

The present invention further provides methods for treating tissue damaged by wound or burn.

In one embodiment, the method comprises the steps of cleaning a site of damaged tissue, and applying topically to the site an antimicrobial and immunostimulating composition comprising a combination of a β-glucan component and a silver-containing component. The method may further include repeated applications of the composition intermittently until healing of the damaged tissue is complete. The topical compositions described above are suitable for use in the method.

In another embodiment, the method comprises the steps of cleaning a site of damaged tissue, and covering the site with a wound dressing comprising a mesh material and a composition comprising an antimicrobially effective and immunostimulating amount of a combination of a β-glucan component and a silver-containing component. The wound dressings described above are suitable for use in the method.

Method for Treating or Repairing Tissue at a Surgical Site

The present invention also provides a method for treating or repairing tissue at a surgical site. The method comprises the step of applying to the surgical site a biocompatible mesh device, the mesh device comprising a mesh matrix and a composition comprising an antimicrobially effective and immunostimulating amount of a combination of a β-glucan component and a silver-containing component. The mesh devices described above are suitable for use in the method. The method may be suitable for treating or repairing tissue at a herniation site, or for other procedures listed above. In one particular application, the method may be suitable where the mesh device is required to provide reinforcement to the tissue. In another application, the method may be suitable where the mesh device is intended to become incorporated into the tissues surrounding a surgical site.

New and varied uses for surgical meshes are being discovered on an ongoing basis and the present invention is to be construed to be applicable to all present and future uses of surgical meshes.

Method for Manufacturing a Medical Composition

A method for manufacturing a medical composition, comprising the step of combining, in an appropriate solvent, a β-glucan component and a silver-containing component in appropriate portions to provide an antimicrobial and immunostimulating composition. Conventional methods may be used for combining the components. The method is suitable for providing the medical compositions described above.

In one embodiment, the method is suitable to provide a composition for topical application.

In another embodiment, the method further comprises the step of coating or impregnating a mesh material to provide a wound dressing.

In yet another embodiment, the method further comprising the step of impregnating a mesh matrix to provide a biocompatible mesh device suitable for treating or repairing tissue at a surgical site.

Zone-of-Inhibition Study

A standard zone-of-inhibition study was performed on the lotion and wound dressing exemplars described above. The zone-of-inhibition test involved placing a quantity of the prepared lotion or wound dressing in a petri dish, which had been cultured with a particular bacterium. The bacteria used in this test included: B. subtilis, B. vulgatus, C. albicans, E. coli, P. aeruginosa, and S. aureus. In each of these tests, the diameter of the prepared lotion or wound dressing placed in the cultured petri dishes was measured and recorded at the outset of the test. On the first, second, and fifth days thereafter the diameter of the zone of inhibition was measured and recorded. The zone of inhibition in this test was defined as the area surrounding the prepared lotion or wound dressing on the petri dish which was uninhabited by the bacteria of the specific culture. Table 1 reports data for the prepared lotion zone-of-inhibition test and Table 2 reports data for the prepared wound dressing zoneof-inhibition test.

TABLE 1

Zone-of-inhibition results using lotion comprising β-glucan and silver

| Bacterium | | Measurement (cm) | Day 1 | Day 2 | Day 5 |
|---|---|---|---|---|---|
| B. subtilis | 1) | 2.05 | 2.93 | 2.88 | 2.75 |
| | 2) | 2.20 | 2.90 | 2.93 | 2.90 |
| | Mean | 2.13 | 2.92 | 2.91 | 2.83 |
| B. vulgatus | 1) | 2.18 | * | 3.35 | 3.38 |
| | 2) | 215 | * | 3.45 | 3.40 |
| | Mean | 2.17 | * | 3.40 | 3.33 |
| C. albicans | 1) | 2.35 | * | 3.70 | 3.70 |
| | 2) | 2.23 | * | 3.55 | 3.65 |
| | Mean | 2.29 | * | 3.63 | 3.68 |
| E. coil | 1) | 2.05 | 2.78 | 2.78 | 2.68 |
| | 2) | 2.18 | 2.75 | 2.70 | 2.65 |
| | Mean | 2.12 | 2.77 | 2.74 | 2.67 |
| P. aeruginosa | 1) | 2.13 | 3.08 | 3.03 | 3.03 |
| | 2) | 2.15 | 3.00 | 3.00 | 3.00 |
| | Mean | 2.14 | 3.04 | 3.02 | 3.02 |
| S. aureus | 1) | 2.10 | 3.08 | 3.08 | 3.05 |
| | 2) | 2.25 | 3.05 | 3.05 | 3.03 |
| | Mean | 2.18 | 3.07 | 3.07 | 3.04 |

TABLE 2

Zone-of-inhibition results using wound dressing
impregnated with β-glucan and silver

| Bacterium | | Measurement (cm) | Day 1 | Day 2 | Day 5 |
|---|---|---|---|---|---|
| B. subtilis | 1) | 2.30 | 3.33 | 3.35 | 3.30 |
| | 2) | 2.13 | 3.08 | 3.03 | 2.98 |
| | Mean | 2.22 | 321 | 3.19 | 3.14 |
| B. vulgatus | 1) | 2.43 | * | 4.13 | 3.98 |
| | 2) | 2.38 | * | 4.25 | 3.93 |
| | Mean | 2.41 | * | 4.19 | 3.96 |
| C. albicans | 1) | 2.23 | * | 3.88 | 3.90 |
| | 2) | 2.20 | * | 3.88 | 3.88 |
| | Mean | 2.22 | * | 3.88 | 3.89 |
| E. coli | 1) | 2.43 | 3.10 | 3.10 | 2.95 |
| | 2) | 2.63 | 2.98 | 2.95 | 2.90 |
| | Mean | 2.53 | 3.04 | 3.03 | 2.93 |
| P. aeruginosa | 1) | 2.20 | 3.33 | 3.35 | 3.28 |
| | 2) | 2.23 | 3.25 | 3.32 | 3.33 |
| | Mean | 2.22 | 3.29 | 3.34 | 3.31 |
| S. aureus | 1) | 2.15 | 3.30 | 3.30 | 3.30 |
| | 2) | 2.10 | 3.25 | 3.25 | 3.20 |
| | Mean | 2.13 | 3.28 | 3.28 | 3.25 |

In explaining the results of the zone-of-inhibition tests it is easiest to refer to a specific example of the tests. Referring first to Table 1, it can be seen that two separate petri dishes were prepared and cultured with the B. subtilis bacterium. Into these prepared petri dishes were placed quantities of the prepared lotion having diameters of 2.05 centimeters and 2.20 centimeters, respectively. After one day, the diameter of the zone of inhibition for these petri dishes was 2.93 centimeters and 2.90 centimeters, respectively. On day two, the zones of inhibition for these lotion samples were 2.88 and 2.93 centimeters in diameter respectively. And on day five, the zones of inhibition for these lotion samples were 2.75 and 2.90 centimeters, respectively.

Referring next to Table 2, two petri dishes were prepared and cultured with the bacterium B. subtilis. Into these prepared petri dishes were placed portions of a wound dressing treated comprising the medical composition having respective diameters of 2.30 and 2.13 centimeters. After one day, the zones of inhibition surrounding the samples of the wound dressing in each of the petri dishes were 3.33 and 3.08 centimeters respectively. After two days, the zones of inhibition surrounding the wound dressing samples were 3.35 centimeters and 3.03 centimeters, respectively. And, after five days, the zones of inhibition surrounding the wound dressing samples were 3.30 and 2.98 respectively.

The results of the zone-of-inhibition tests are indicative of a strong antimicrobial effect for both the prepared lotion and the prepared wound dressing. Similar results are observed for a zone-of-inhibition test when a yeast-derived β-glucan is used in a medical composition as described herein.

In contrast, for a zone-of-inhibition test where only β-glucan is present in either a composition or incorporated into a mesh device, no inhibition of bacteria is observed. Furthermore, it has been observed that the presence of β-glucan, as a microbial nutrient, actually promotes bacterial growth.

In other words, β-glucan does not provide antimicrobial activity. The results of the zone-of-inhibition tests described above indicate that β-glucan does not interfere with the antimicrobial activity that can be provided by a silver-containing component, even though β-glucan will promote growth of bacteria. Therefore, the combination of a silver-containing component and a β-glucan component can provide antimicrobial and immunostimulating properties to a medical composition.

The invention described above may be embodied in other forms without departing from the spirit or essential characteristics thereof. The embodiments disclosed in this application are to be considered in all respects as illustrative and not restrictive. The scope of the invention is indicated by the appended claims rather than by the foregoing description and all changes, which come within the meaning and range of equivalency of the claims, are embraced therein.

The invention claimed is:

1. A method for treating a wound or burn, comprising the steps of:
   a) cleaning a site of a wound or burn; and
   b) topically covering the site with an antimicrobial and irnmunostimulating unguent, cream, gel, emollient, lotion or oil comprising a combination of an oat-derived, β-glucan component providing an immune response to improve tissue regeneration and speed recovery and a silver-containing component providing an effective zone of inhibition of about 2 mm or more against B. subtitis, B. vulgatus, C. albicans, E. coil, P. aeruginosa and S. aureus, wherein the unguent, cream, get, emollient, lotion or oil provides an antimicrobial and immunostimulating effect over a period of time at the wound or burn site.

2. The method of claim 1, and including repeating application of the composition intermittently until healing of the wound or burn is complete.

3. The method of claim 1, wherein the combination is applied to the site for a period of time of more than two days.

4. The method of claim 1, wherein the combination is applied to the site for a period of time of more than five days.

5. The method of claim 1, wherein about 0.01% to about 50% by weight of the composition is the oat derived β-glucan component, and about 0.01% to about 15% by weight of the composition is the silver-containing component.

6. The method of claim 1, wherein the oat derived β-glucan having has about 70% (1-4) linkages and about 30% (1-3) linkages.

7. The method of claim 1, wherein the silver-containing component is elemental silver, silver nitrate, silver bromide, silver sulfate, silver fluoride, silver iodide, silver chloride, silver oxides, silver protein, silver lactate, silver citrate, or silver sulfadiazine.

8. The method of claim 1, wherein the composition includes about 10 parts by weight of oat derived β-glucan to about 3 parts by weight silver nitrate.

9. The method of claim 1, wherein the composition further comprises collagenic protein.

10. The method of claim 9, wherein about 0.1% to about 20% by weight of the composition is the collagenic protein.

11. The method of claim 1, wherein the composition is a cream comprising 0.05-0.25 wt % oat derived β-glucan, 10-20 wt% ointment base, 5-15 wt % humectant, 0.5-3 wt % viscosity agent, 1-3 wt % stiffener, 0.05- 0.2 wt % emulsifier, 0.05-1 wt % preservative, 0-4 wt % plasticizer, 0.01-0.4 wt % silver sulfate, and 60-80 wt % solvent.

12. The method of claim 1, wherein the composition is an ointment cream comprising 0.05-0.25 wt % oat derived β-glucan, 0.01-0.4 wt % silver sulfate, and 50-99.5 wt % ointment base.

13. The method of claim 1, wherein the composition is a lotion comprising 0.05-0.25 wt % oat derived β-glucan, 2.5-10 wt % petrolatum, 30-50 wt % mineral oil, 5-15 wt % emulsifiers, 0-20 wt % ointment base, 0-2 wt % stiffening agent, 0.01-0.4 wt % silver sulfate, and 15-25 wt % water.

14. A method for treating a wound or burn, comprising the steps of:

a) cleaning a site of a wound or burn; and b) covering the site with a wound dressing to provide an antimicrobial and immunostimulating effect at the wound or burn site over a period of time, wherein the wound dressing comprises a mesh material and a composition comprising a combination of an oat derived β-glucan component providing an immune response to improve tissue regeneration and speed recovery and a silver-containing component providing an effective zone of inhibition of about 2 mm or more against *B. subtilis, B. vulgatus, C. albicans, E. coli, P. aeuroginosa* and *S. aureus*.

15. The method of claim 14, wherein the composition is applied to the mesh material before topically applied to the wound or burn site.

16. The method of claim 14, wherein the mesh material comprises a synthetic material selected from the group consisting of polyester, polypropylene, polytetrafluoroethylene, expanded polytetrafluoroethylene, polyurethane, polyethylene terephthalate, polyglycolic acid, polyglactin, and silicone.

17. The method of claim 14, wherein the mesh material comprises a material derived from a human source or an animal source.

18. The method of claim 14, wherein the wound dressing covers the site for a time period of more than two days.

19. The method of claim 14, wherein the wound dressing covers the site for a time period of more than five days.

20. The method of claim 14, wherein the wound dressing comprises about 50-99.99 wt % synthetic mesh material, 3-14 wt % oat derived β-glucan component, and 0.03-15 wt % silver-containing component.

21. A method for treating a wound or burn, comprising the steps off a) cleaning a site of a wound or burn; and b) covering the site with a composition or a wound dressing comprising the composition, wherein the composition comprises an antimicrobially effective and immunostimulating amount of a combination of an oat derived β-glucan component and a silver-containing component and wherein the composition delivers elemental silver or silver ion into the wound or burn and provides an effective zone of inhibition of about 2 mm or more against *B. subtilis, B. vulgatus, C. albicans, E. coli, P. aeruginosa* and *S. aureus*.

* * * * *

UNITED STATES PATENT AND TRADEMARK OFFICE
CERTIFICATE OF CORRECTION

PATENT NO. : 8,231,894 B2
APPLICATION NO. : 13/156566
DATED : July 31, 2012
INVENTOR(S) : Barbara K. Klein et al.

Page 1 of 1

It is certified that error appears in the above-identified patent and that said Letters Patent is hereby corrected as shown below:

Column 12, Line 22
Claim 1
"E. coil" should be -- E. coli --

Column 12, Line 23
Claim 1
"get" should be -- gel --

Column 12, Lines 38-39
Claim 6
"β- glucan having has about" should be -- β-glucan has about --

Signed and Sealed this
Twenty-third Day of October, 2012

David J. Kappos
*Director of the United States Patent and Trademark Office*